(12) United States Patent
Speronello et al.

(10) Patent No.: US 8,137,581 B2
(45) Date of Patent: Mar. 20, 2012

(54) CHLORINE DIOXIDE RELEASING COMPOSITE ARTICLE

(75) Inventors: Barry K. Speronello, Montgomery Township, NJ (US); Linda Hratko, Colonia, NJ (US); Michael S. Cochran, Morris Plains, NJ (US)

(73) Assignee: BASF Corporation, Florham Park, NJ (US)

( * ) Notice: Subject to any disclaimer, the term of this patent is extended or adjusted under 35 U.S.C. 154(b) by 689 days.

(21) Appl. No.: 10/902,735

(22) Filed: Jul. 29, 2004

(65) Prior Publication Data

US 2006/0024369 A1 Feb. 2, 2006
US 2009/0238872 A9 Sep. 24, 2009

Related U.S. Application Data

(60) Provisional application No. 60/492,431, filed on Aug. 4, 2003.

(51) Int. Cl.
*A62D 3/30* (2007.01)
*C01B 11/10* (2006.01)

(52) U.S. Cl. .......................... 252/187.23; 252/187.21
(58) Field of Classification Search ............. 252/187.23, 252/187.21; 514/772.4
See application file for complete search history.

(56) References Cited

U.S. PATENT DOCUMENTS

| | | | |
|---|---|---|---|
| 4,585,482 A * | 4/1986 | Tice et al. .................. | 106/15.05 |
| 5,545,450 A * | 8/1996 | Andersen et al. ............ | 428/34.5 |
| 5,719,100 A * | 2/1998 | Zahradnik et al. ............ | 502/417 |
| 6,046,243 A * | 4/2000 | Wellinghoff et al. ....... | 514/772.3 |
| 6,277,408 B1 * | 8/2001 | Wellinghoff et al. ......... | 424/473 |
| 6,294,108 B1 | 9/2001 | Speronello et al. ....... | 252/187.21 |
| 6,479,037 B1 * | 11/2002 | Montgomery .................. | 424/53 |
| 6,776,998 B1 * | 8/2004 | Corrigan ....................... | 424/443 |
| 7,087,190 B2 * | 8/2006 | Hei et al. .................. | 252/187.21 |
| 2003/0235605 A1 * | 12/2003 | Lelah et al. ................... | 424/443 |
| 2005/0106380 A1 * | 5/2005 | Gray et al. ................... | 428/323 |
| 2006/0216496 A2 * | 9/2006 | Gray et al. ................... | 428/323 |

FOREIGN PATENT DOCUMENTS

| | | |
|---|---|---|
| CN | 1094698 | 11/1994 |
| CN | 1104610 A | 7/1995 |
| EP | 0 611 162 A1 | 8/1994 |
| WO | WO 00/69775 | 11/2000 |
| WO | WO 03/056951 A2 | 7/2003 |

OTHER PUBLICATIONS

Lewis, Richard J., Sr. (2002). Hawley's Condensed Chemical Dictionary (14th Edition). "Polyethylene glycol", John Wiley & Sons. Online version available at: http://www.knovel.com/knovel2/Toc.jsp?BookID=704&VerticalID=0.*

* cited by examiner

*Primary Examiner* — Peter F Godenschwager
(74) *Attorney, Agent, or Firm* — Bernard Lau

(57) ABSTRACT

A composite article that includes a $ClO_2$-producing material integrated into an organic matrix and methods of using the same are described. The organic matrix of the composite article is formable at a temperature under about 150° C., permits contact between an activating stimulus (e.g., water vapor and/or electromagnetic energy) and the $ClO_2$-producing material when the composite article is exposed to the activating stimulus, and is permeable to $ClO_2$.

20 Claims, No Drawings

CHLORINE DIOXIDE RELEASING COMPOSITE ARTICLE

FIELD OF THE INVENTION

This invention relates to a device which will produce chlorine dioxide gas when exposed to an activating stimulus such as ambient humidity or light, and methods of using the same.

BACKGROUND OF THE INVENTION

The prior art discloses a variety of powdered compositions that produce $ClO_2$ gas under a variety of conditions. Included in these are materials for the controlled sustained release of ClO2 (CSR materials), which release $ClO_2$ when exposed to water vapor. Also included are materials disclosed by which produce $ClO_2$ when exposed to light.

It is desirable for ease of use and disposal for such materials to be contained or packaged in a manner that contains the powder in a porous pouch (i.e., a sachet) or for it to be extruded into a polymer matrix film, such as polyethylene. In this manner the user is protected from direct contact with the powder, and spent powder may be more readily removed from the area that was treated.

Unfortunately, sachets are relatively bulky and expensive to fabricate, and in small sizes are very light and difficult to handle. As a result, the cost of packaging powders in small sachets (less than about 2 grams in size) is often impractically high.

Extruded polymer sheet material can be relatively less expensive to produce in small sizes, because the sheet may be produced in a large economical size, and then smaller size pieces may be inexpensively cut from the larger sheet. However, due to the low decomposition temperature of the chlorite anion that is incorporated into all $ClO_2$ producing materials, the extrusion temperature of $ClO_2$-releasing polymer sheet must be no higher than about 150-160° C. If the temperature is above that, then the amount of chlorite that is lost by decomposition during extrusion can be unacceptably high. This has limited the choice of polymer matrices to those comprising a substantial amount of relatively low melting, low density polyethylene. But polyethylene is an undesirable matrix material because it is not highly permeable to water vapor used to initiate the release of chlorine dioxide from most chlorine dioxide-releasing materials. Plus the extrusion temperature of polyethylene is about 150 degrees C., so it is right on the borderline where decomposition of chlorite anion can occur. Since chlorite decomposition can lead to explosive oxidation of the polyethylene, such extruded sheet materials typically contain lower concentrations of chlorite anion than many powdered versions. Lower chlorite content, in turn, limits their maximum yield of $ClO_2$.

SUMMARY OF THE INVENTION

Generally, the invention relates to composite articles comprising a material capable of producing $ClO_2$ upon exposure to an activating stimulus that is integrated into an organic matrix, and methods of using the article. The organic matrix is formable at a temperature below about 150° C., preferably below about 135° C., and most preferably below about 110° C. When the composite article is exposed to an activating stimulus, such as water or light, the organic matrix permits at least some contact between the $ClO_2$-producing material and the activating stimulus, which in turn causes the material to generate $ClO_2$. The organic matrix is also permeable to $ClO_2$ so as to allow at least a portion of $ClO_2$ generated by the $ClO_2$-producing material to escape the composite article. Preferably the article is stable during storage prior to exposure to the stimulus.

DETAILED DESCRIPTION OF THE PREFERRED EMBODIMENTS

The invention relates to a composite article comprising a $ClO_2$-producing material integrated into an organic matrix, and methods of using the same.

The $ClO_2$-producing material is any material or combination of materials that is capable of generating $ClO_2$ upon exposure to some activating stimulus. The activating stimulus may be water vapor, electromagnetic energy, or any other trigger that effects the formation of $ClO_2$ by the $ClO_2$-producing material. Typically, $ClO_2$-producing materials comprise a chlorite-containing compound, such as sodium chlorite, and an acidifying agent. Examples of $ClO_2$-producing materials are described in U.S. Pat. No. 6,294,108 and WO 03/056951 A2, both incorporated herein by reference.

The organic matrix contains at least one organic material and: a) is formable at temperatures below about 150° C., preferably below about 135° C., more preferably below about 110° C.; b) permits at least some contact between an activating stimulus and the $ClO_2$-producing material when the composite article is exposed to the activating stimulus so as to enable generation of $ClO_2$; and c) is permeable to $ClO_2$. The low temperature formability of the organic matrix is compatible with temperature-sensitive $ClO_2$-producing materials. When exposed to an activating stimulus, the organic matrix allows the activating stimulus to contact an integrated $ClO_2$-producing material, and permits the resulting $ClO_2$ to escape into the space surrounding the article.

One class of materials that may be suitable for the organic matrix is low melting molecular solids. In particular, low melting hydrophilic molecular solids. Examples of low melting molecular solid materials are polyethylene glycol wax (such as that sold under the trade name CARBOWAX by the Dow Chemical Co.), mixtures of polyethylene glycol wax with paraffin wax, stearic acid, and mixtures of polyethylene glycol wax with stearic acid. An organic matrix comprising only paraffin wax as the organic material is preferably used with a humidity-activated $ClO_2$-releasing material and with a pore former incorporated into the formulation to facilitate humidity intrusion.

Another class of materials suitable for the organic matrix are low melting thermoformable or thermosetting functionalized polymers, such as EVA (ethylene vinyl acetate). These are commonly used in the formulation of hot melt glue products that soften and flow (i.e. can be extruded) at relatively low temperatures. Other hot melt glue type formulations are also satisfactory for this purpose. If $ClO_2$ release is to be initiated by exposure to light, it is preferred that the matrix material be effectively transparent to the light.

The composite article may be formed by combining the $ClO_2$-releasing material(s) with the organic matrix material(s), heating to a temperature that is below 150° C. to soften or melt the matrix material(s), and extruding the mixture into rods, sheet, pellets, or the like. Alternatively, the matrix material(s) may be heated to a temperature below 150° C. and softened/melted prior to combination with the $ClO_2$-producing material.

Alternatively, the composite article may be formed by casting a mixture into a mold and cooling; by coating a mixture on a flat surface to form a thin sheet (such as by the doctor blade process); or by passing a mixture through the nip space between two rollers to form a sheet. Likewise, any of several other methods known to those in the art may be used to form an article.

The composite article may contain other constituents that provide desired characteristics. For example, fibrous material may be added to the composite to increase stiffness and strength, or plasticizers may be added to increase flexibility. Pore formers, such as silica gel and diatomaceous earth, may be added to increase the porosity of the article. Increased porosity could facilitate the passage of water vapor into, and/or $ClO_2$ out of, the article. Coloring and fragrances may be added to enhance aesthetics. Desiccants may be added to limit water exposure during storage.

The composite article may be used wherever $ClO_2$ would be desired and exposure to an activating stimulus would occur. Some specific applications include: food shelf-life extension, microbial deterioration protection of good (e.g., shoes) during transportation and/or storage, microbial-resistant packaging, deodorizing devices, and deodorizing coatings.

A non-limiting example of a preferred embodiment will now be described.

EXAMPLE

Thirteen point three (13.3) grams of chlorine dioxide releasing powder similar to that described in example 7 of U.S. Pat. No. 6,294,108 was mixed into 20 grams of melted polyethylene glycol wax (CARBOWAX 4000 brand) at a temperature below 100° C. Five point three (5.3) grams of that mixture was poured into a small aluminum dish to produce a disk approximately 2 inches in diameter and ⅛ inch thick. This disk was tested for the release of chlorine dioxide at 80% relative humidity using the test method described in U.S. Pat. No. 6,294,108, and it produced 5 ppm of $ClO_2$ at about 20 hours.

What is claimed is:

1. A composite article comprising a $ClO_2$-producing material integrated into a hydrophilic organic matrix and optionally one of fibrous materials, plasticizers, pore formers, colorings, fragrances, desiccants, or combination thereof,
   wherein the $ClO_2$-producing material comprises a chlorite-containing compound and an acidifying agent in an intimate physical mixture,
   wherein the composite article releases $ClO_2$ when contacted by an activating stimulus comprising water vapor or water, and wherein light is not an activating stimulus for the composite article, and
   wherein the hydrophilic organic matrix:
   a) is formable at a temperature below about 150° C.;
   b) permits at least some contact between the activating stimulus and the $ClO_2$-producing material when the composite article is exposed to the activating stimulus; and
   c) is permeable to $ClO_2$.

2. The composite article of claim 1, wherein the hydrophilic organic matrix is formable at a temperature below about 135° C.

3. The composite article of claim 1, wherein the hydrophilic organic matrix is formable at a temperature below about 110° C.

4. The composite article of claim 1, wherein the hydrophilic organic matrix comprises a thermoformable or thermosetting polymer.

5. The composite article of claim 1, wherein the hydrophilic organic matrix consists of ethylene vinyl acetate.

6. The composite article of claim 1, wherein the composite article consists of the $ClO_2$-producing material integrated into the hydrophilic organic matrix and at least one of plasticizers, fibrous materials, or combinations thereof.

7. The composite article of claim 1, wherein the composite article consists of the $ClO_2$-producing material integrated into the hydrophilic organic matrix and pore formers.

8. The composite article of claim 1, wherein the composite article consists of the $ClO_2$-producing material integrated into the hydrophilic organic matrix, and one of colorings, fragrances, or combinations thereof.

9. The composite article of claim 1, wherein the composite article consists of the $ClO_2$-producing material integrated into the hydrophilic organic matrix, desiccants, and optionally one of fibrous materials, plasticizers, pore formers, colorings, fragrances, or combination thereof.

10. The composite article of claim 1, wherein the composite article consists of the $ClO_2$-producing material integrated into the hydrophilic organic matrix and desiccants.

11. The composite article of claim 1, wherein the composite article is formed by extruding the hydrophilic organic matrix and the $ClO_2$-producing material into rods, sheet, or pellets.

12. The composite article of claim 1, wherein the composite article is formed by casting the hydrophilic organic matrix and the $ClO_2$-producing material in a mold.

13. The composite article of claim 1, wherein the composite article is formed by coating the hydrophilic organic matrix and the $ClO_2$-producing material on a flat surface.

14. The composite article of claim 1, wherein the composite article is formed by passing the hydrophilic organic matrix and the $ClO_2$-producing material through a nip space between two rollers to form a sheet.

15. A method of producing chlorine dioxide, comprising exposing the composite article of claim 1 to water vapor.

16. The composite article of claim 1, wherein the hydrophilic organic matrix consists of polyethylene glycol and stearic acid or the hydrophilic organic matrix consists of polyethylene glycol, paraffin wax, and stearic acid.

17. The composite article of claim 1, wherein the hydrophilic organic matrix consists of polyethylene glycol.

18. A composite article consisting of a $ClO_2$-producing material consisting of a chlorite-containing compound and an acidifying agent in an intimate physical mixture integrated into an organic matrix and optionally one of fibrous materials, plasticizers, pore formers, colorings, fragrances, desiccant, or combination thereof,
   wherein the composite article releases $ClO_2$ when contacted by an activating stimulus comprising water vapor or water, and wherein light is not an activating stimulus for the composite article, and
   wherein the organic matrix:
   a) is formable at a temperature below about 150° C.;
   b) permits at least some contact between the activating stimulus and the $ClO_2$-producing material when the composite article is exposed to the activating stimulus; and
   c) is permeable to $ClO_2$.

19. The composite article of claim 18, wherein the organic matrix consists of polyethylene glycols, paraffin wax, a mixture of polyethylene glycol, paraffin wax, and stearic acid, a mixture of polyethylene glycol and stearic acid, or ethylene vinyl acetates.

20. The composite article of claim 18, wherein the composite article consists of the $ClO_2$-producing material integrated into the organic matrix, desiccants, and optionally one of fibrous materials, plasticizers, pore formers, colorings, fragrances, or combination thereof.

* * * * *